United States Patent [19]
Duplantier

[11] Patent Number: 5,596,013
[45] Date of Patent: Jan. 21, 1997

[54] DIHYDRO PYRAZOLOPYRROLES

[75] Inventor: Allen J. Duplantier, New York, N.Y.

[73] Assignee: Pfizer Inc, New York, N.Y.

[21] Appl. No.: 632,301

[22] Filed: Apr. 15, 1996

Related U.S. Application Data

[63] Continuation of Ser. No. 181,690, Jan. 14, 1994, Pat. No. 5,508,300.

[51] Int. Cl.$^6$ .................. A61K 31/415; C07D 487/04
[52] U.S. Cl. ........................ 514/403; 548/360.5
[58] Field of Search ................. 548/360.5; 514/403

[56] References Cited

PUBLICATIONS

Nakano et al, *Chemical Abstracts*, vol. 121, No. 157661f (1994).
Elguero et al, *Chemical Abstracts*, vol. 75, 48974 (1971).

*Primary Examiner*—Robert W. Ramsuer
*Attorney, Agent, or Firm*—Peter C. Richardson; Paul H. Ginsburg; Gezina Holtrust

[57] ABSTRACT

The compounds of the formula

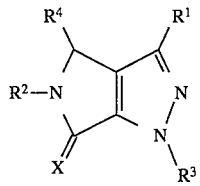

and the pharmaceutically acceptable salts thereof; wherein $X_1$, $R^1$, $R^2$, $R^3$ and $R^4$ are as defined herein, are inhibitors of PDE IV and the production of tumor necrosis factor. As such, they are active in the treatment of inflammatory diseases, shock etc.

9 Claims, No Drawings

DIHYDRO PYRAZOLOPYRROLES

This is a continuation of application Ser. No. 08/181,690, filed on Jan. 14, 1994 now U.S. Pat. No. 5,508,300.

BACKGROUND OF THE INVENTION

This invention relates to a series of dihydropyrazolopyrroles which are selective inhibitors of phosphodiesterase (PDE) type IV or the production of tumor necrosis factor (TNF), and as such are useful in the treatment of, respectively, inflammatory and other diseases; and AIDS, septic shock and other diseases involving the production of TNF.

This invention also relates to a method of using such compounds in the treatment of the above diseases in mammals, especially humans, and to pharmaceutical compositions containing such compounds.

Since the recognition that cyclic adenosine phosphate (AMP) is an intracellular second messenger, E. W. Sutherland, and T. W. Rail, Pharmacol. Rev., 12,265, (1960), inhibition of the phosphodiesterases has been a target for modulation and, accordingly, therapeutic intervention in a range of disease processes. More recently, distinct classes of PDE have been recognized, J. A. Beavo et al., TiPS, 11,150, (1990), and their selective inhibition has led to improved drug therapy, C. D. Nicholson, M. S. hahid, TiPS, 12, 19, (1991). More particularly, it has been recognized that inhibition of PDE type IV can lead to inhibition of inflammatory mediator release, M. W. Verghese et al., J. Mol. Cell Cardiol., 12 (Suppl. II), S 61, (1989) and airway smooth muscle relaxation (T. J. Torphy in "Directions for New Anti-Asthma Drugs," eds S. R. O'Donnell and C. G. A. Persson, 1988, 37 Birkhauser-Verlag). Thus, compounds that inhibit PDE type IV, but which have poor activity against other PDE types, would inhibit the release of inflammatory mediators and relax airway smooth muscle without causing cardiovascular effects or antiplatelet effects.

TNF is recognized to be involved in many infectious and auto-immune diseases, W. Friers, FEBS Letters, 285, 199, (1991). Furthermore, it has been shown that TNF is the prime mediator of the inflammatory response seen in sepsis and septic shock, C. E. Spooner et al., Clinical Immunology and Immunopathology, 62, S11, (1992).

SUMMARY OF THE INVENTION

The present invention relates to compounds of the formula

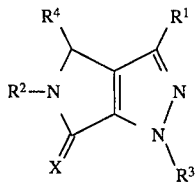

and the pharmaceutically acceptable salts thereof; wherein X is oxygen or two hydrogens; $R^1$ is hydrogen, $C_1$–$C_7$ alkyl, $C_2$–$C_3$ alkenyl, phenyl, $C_3$–$C_5$ cycloalkyl or methylene($C_3$–$C_5$ cycloalkyl) wherein each alkyl, phenyl or alkenyl group may be substituted with one or two methyl, ethyl or trifluoromethyl, or up to three halogens; $R^2$ and $R^3$ are each independently selected from the group consisting of hydrogen; $C_1$–$C_{14}$ alkyl; ($C_1$–$C_7$ alkoxy)($C_1$–$C_7$ alkyl)—; $C_2$–$C_{14}$ alkenyl; —$(CH_2)_n(C_3$–$C_5$ cycloakyl) wherein n is 0, 1 or 2; a $(CH_2)_n(C_4$–$C_7$ heterocyclic group) wherein n is 0, 1 or 2, containing as the heteroatom one of oxygen, sulphur, sulphonyl or $NR^5$ wherein $R^5$ is hydrogen, or $C_1$–$C_4$ alkyl; or a group of the formula

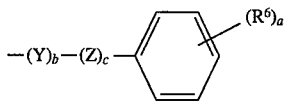

wherein a is an integer from 1 to 4; b and c are 0 or 1; $R^6$ is hydrogen, hydroxy, $C_1$–$C_5$ alkyl, $C_2$–$C_5$ alkenyl, $C_1$–$C_5$ alkoxy, $C_1$–$C_6$ cycloalkoxy, halogen, trifluoromethyl, nitro, $CO_2R^7$, $CONR^7R^8$, $NR^7R^8$, or $SO_2NR^7R^8$ wherein $R^7$ and $R^8$ are each independently hydrogen or $C_1$–$C_4$ alkyl; Z is oxygen, sulphur, sulphonyl or $NR^9$ wherein $R^8$ is hydrogen or $C_1$–$C_4$ alkyl; and Y is $C_1$–$C_5$ alkylene or $C_2$–$C_6$ alkenylene which may be substituted with one or two $C_1$–$C_7$ alkyl or $C_1$–$C_7$ cycloalkyl; wherein each of said alkyl, alkenyl, cycloalkyl, alkoxyalkyl or heterocyclic group may be substituted with one to fourteen substituents $R_{10}$ selected from the group consisting of methyl, ethyl, trifluoromethyl and halogen; and $R^4$ is hydrogen, $C_1C_7$ alkyl, phenyl, $C_3$–$C_5$ cycloalkyl, or methylene ($C_3$–$C_5$ cycloalkyl) wherein each alkyl or phenyl group may be substituted with one or two methyl, ethyl or trifluoromethyl, or up to three halogens.

More specific compounds of the invention are those wherein X is oxygen, those wherein $R^1$ is $C_1$–$C_7$ alkyl, those wherein $R^4$ is hydrogen, those wherein $R^3$ is $C_1$–$C_6$ alkyl; phenyl substituted by one or two halogen; cyclopentyl, or methylenecyclopropyl; and those wherein $R^2$ is hydrogen, $C_1$–$C_6$ alkyl, or phenyl which may be substituted by $C_1$–$C_5$ alkyl, $C_1$–$C_5$ alkoxy or COOH.

Other more specific compounds of the invention are those wherein X is oxygen, $R^1$ is $C_1$–$C_7$ alkyl, $R^4$ is hydrogen, $R^3$ is $C_1$–$C_6$ alkyl; phenyl substituted by one or two halogen; cyclopentyl, or methylenecyclopropyl, and $R_2$ is hydrogen, $C_1$–$C_6$ alkyl or phenyl which may be substituted with $C_1$–$C_5$ alkyl, $C_1$–$C_5$ alkoxy or COOH.

The present invention further relates to a pharmaceutical composition for the inhibition of phosphodiesterase (PDE) type IV and the production of tumor necrosis factor (TNF) comprising a pharmaceutically effective amount of a compound according to formula I or a pharmaceutically acceptable salt thereof, and a pharmaceutically acceptable carrier.

The present invention further relates to a method for the inhibition of phosphodiesterase (PDE) type IV and the production of tumor necrosis factor (TNF) by administering to a patient an effective amount of a compound according to formula I or a pharmaceutically acceptable salt thereof.

The present invention further relates to a method of treating an inflammatory condition in mammals by administering to said mammal an antiinflammatory amount of a compound of the formula I or a pharmaceutically acceptable salt thereof.

According to the invention, an inflammatory condition includes asthma, arthritis, bronchitis, chronic obstructive airways disease, psoriasis, allergic rhinitis, and dermatitis.

The present invention further relates to a pharmaceutical composition for the treatment of AIDS, septic shock and other diseases involving the production of TNF comprising a pharmaceutically effective amount of a compound according to formula I or a pharmaceutically acceptable salts thereof together with a pharmaceutically acceptable carrier.

This invention further relates to a method of treating or preventing an inflammatory condition, or AIDS, septic shock and other diseases involving the production of TNF by administering to a patient an effective amount of a compound according to formula I or a pharmaceutically acceptable salt thereof.

DETAILED DESCRIPTION OF THE INVENTION

The term "halogen", as used herein, includes chloro, fluoro and bromo.

Unless indicated otherwise, the alkyl, alkoxy and alkenyl groups referred to herein may be straight chain or if comprising three or more carbons may be straight chained or branched.

$R^1$, $R^2$, $R^3$ and $R^4$, as used herein are as defined above with reference to formula I, unless otherwise indicated.

The compounds of the invention of formula I may be prepared as depicted in Scheme 1.

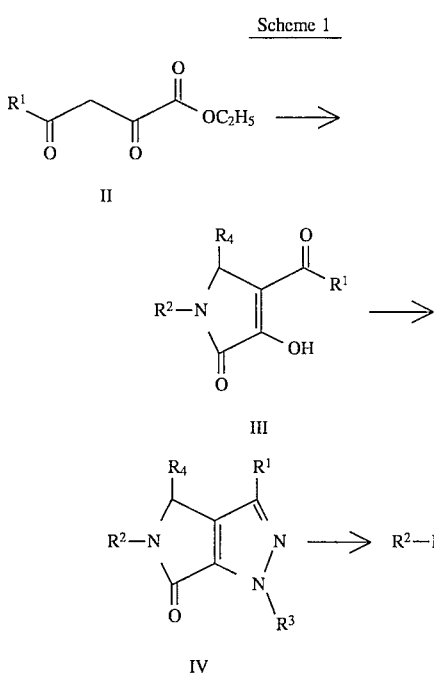

The ethyl 2,4-dioxoalkanoate of formula II is converted to the corresponding N—(R2)-2,5-dihydropyrrole compound III by subjecting II to the conditions of a Mannich reaction using compounds of the formulae $R_2NH_2$, and $R_4C(O)H$, and concentrated hydrogen chloride in alcohol. The mixture is heated to reflux for 2 to about 6 hours, preferably about 3 hours.

The compound of formula III is converted to 4,6-dihydro-1H-pyrazolo[3,4-c]pyrrole compound IV by reacting III with a hydrazine hydrochloride of the formula $R^3HNNH_2 \cdot HCl$ and a sodium $C_1$–$C_6$ alkoxide in an anhydrous polar protic solvent. The preferred sodium alkoxide is sodium methoxide and the preferred anhydrous polar solvent is anhydrous ethanol. The reaction mixture is heated to reflux for about 9 hours to about 20 hours, preferably about 16 hours.

The compound of formula IV is converted to the corresponding compound of formula V by reacting IV with a reducing agent, preferably lithium aluminum hydride, in a non-polar aprotic solvent, preferably ether. The majority of the solvent is removed by distillation, and the remaining mixture is diluted with a higher boiling non-polar aprotic solvent, preferably toluene. The reaction is heated to reflux for about 12 hours to about 24 hours, preferably 24 hours.

The compounds of formula IV wherein $R_4$ is hydrogen may alternatively be prepared as depicted in Scheme 2.

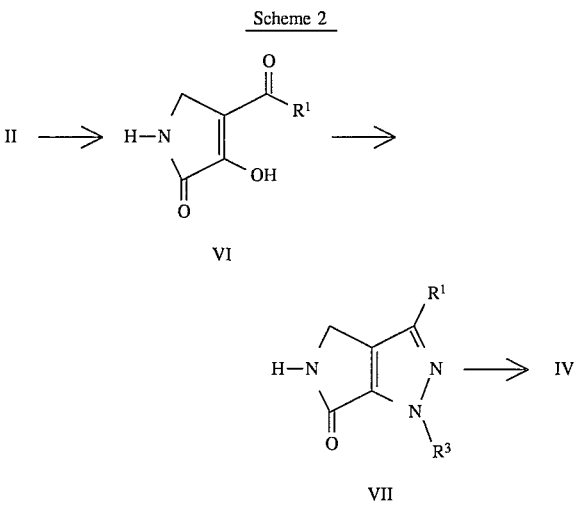

The compound II is subjected to the conditions of a Mannich reaction using dimethylmethylene ammonium chloride in a non-polar aprotic solvent, preferably acetonitrile. The mixture is cooled to about –40° C. and treated with ammonia gas for about 5 minutes and is slowly warmed to about 5° C. over about 1 hour before treating with concentrated ammonium hydroxide. The compound VI so formed is reacted as described above for the conversion of compound III to compound IV. The compound of formula VII so formed is converted to compound IV by reaction with a base, such as sodium hydride, in a polar aprotic solvent such as tetrahydrofuran or dimethylformamide. The reaction is generally conducted at reflux for about 30 minutes to about one hour, preferably about 45 minutes. The mixture is then cooled to ambient temperature and treated with the appropriate $R_3$– halide at ambient temperature. The mixture is stirred at reflux for about 1 hour to 24 hours, preferably about 16 hours.

Pharmaceutically acceptable acid addition salts of the compounds of this invention include, but are not limited to, those formed with HCl, HBr, $HNO_3$, $H_2SO_4$, $H_3PO_4$, $CH_3SO_3H$, p-$CH_3C_6H_4SO_3H$, $CH_3CO_2H$, gluconic acid, tartaric acid, maleic acid and succinic acid. Pharmaceutically acceptable cationic salts of the compounds of this invention of formula I wherein $R^6$ is $CO_2R^7$ and $R^7$ is hydrogen include, but are not limited to, those of sodium, potassium, calcium, magnesium, ammonium, N,N'-dibenzylethylenediamine, N-methylglucamine (meglumine), ethanolamine and diethanolamine.

For administration to humans in the curative or prophylactic treatment of inflammatory diseases, oral dosages of a compound of formula I or the pharmaceutically acceptable salts thereof (the active compounds) are generally in the range of from 0.1–100 mg daily for an average adult patient (70 kg). Thus for a typical adult patient, individual tablets or capsules contain from 0.1 to 50 mg of active compound, in a suitable pharmaceutically acceptable vehicle or carrier. Dosages for intravenous administration are typically within the range of 0.1 to 10 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For administration to humans for the inhibition of TNF, a variety of conventional routes may be used including orally, parenterally and optically. In general, the active compound will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration will, in any event, determine the appropriate dose for the individual subject.

For human use, the active compounds of the present invention can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules or ovales either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substance; for example, enough salts or glucose to make the solution isotonic.

Additionally, the active compounds may be administered topically when treating inflammatory conditions of the skin and this may be done by way of creams, jellies, gels, pastes, and ointments, in accordance with standard pharmaceutical practice.

The ability of the compounds of formula I or the pharmaceutically acceptable salts thereof to inhibit PDE IV may be determined by the following assay.

Thirty to forty grams of human lung tissue is placed in 50 ml of pH 7.4 Tris/phenylmethylsulfonyl fluoride (PMSF)/sucrose buffer and homogenized using a Tekmar Tissumizer® (Tekmar Co., 7143 Kemper Road, Cincinnati, Ohio 45249) at full speed for 30 seconds. The homogenate is centrifuged at 48,000×g for 70 minutes at 4° C. The supernatant is filtered twice through a 0.22 μm filter and applied to a Mono-Q FPLC column (Pharmacia LKB Biotechnology, 800 Centennial Avenue, Piscataway, N.J. 08854) pre-equilibrated with pH 7.4 Tris/PMSF Buffer. A flow rate of 1 ml/minute is used to apply the sample to the column, followed by a 2 ml/minute flow rate for subsequent washing and elution. Sample is eluted using an increasing, step-wise NaCl gradient in the pH 7.4 Tris/PMSF buffer. Eight ml fractions are collected. Fractions are assayed for specific $PDE_{IV}$ activity determined by [3H]cAMP hydrolysis and the ability of a known $PDE_{IV}$ inhibitor (e.g. rolipram) to inhibit that hydrolysis. Appropriate fractions are pooled, diluted with ethylene glycol (2 ml ethylene glycol/5 ml of enzyme prep) and stored at −20° C. until use.

Compounds are dissolved in dimethylsulfoxide (DMSO) at a concentration of 10 mM and diluted 1:25 in water (400 μM compound, 4% DMSO). Further serial dilutions are made in 4% DMSO to achieve desired concentrations. The final DMSO concentration in the assay tube is 1%. In duplicate the following are added, in order, to a 12×75 mm glass tube (all concentrations are given as the final concentrations in the assay tube).

i) 25 μl compound or DMSO (1%, for control and blank)

ii) 25 μl pH 7.5 Tris buffer iii) [$^3$H]cAMP (1 μM)

iv) 25 μl PDE IV enzyme (for blank, enzyme is preincubated in boiling water for 5 minutes)

The reaction tubes are shaken and placed in a water bath (37° C.) for 20 minutes, at which time the reaction is stopped by placing the tubes in a boiling water bath for 4 minutes. Washing buffer (0.5 ml, 0.1M 4-(2-hydroxyethyl)-1-piperazine-ethanesulfonic acid (HEPES)/0.1M naci, pH 8.5) is added to each tube on an ice bath. The contents of each tube are filed to an AFF-Gel 601 column (Biorad Laboratories, P.O. Box 1229, 85A Marcus Drive, Melvile, N.Y. 11747) (boronate affinity gel, 1 ml bed volume) previously equilibrated with washing buffer. [$^3$H]cAMP is washed with 2×6 ml washing buffer, and [$^3$H]5'AMP is then eluted with 4 ml of 0.25M acetic acid. After vortexing, 1 ml of the elution is added to 3 ml scintillation fluid in a suitable vial, vortexed and counted for [3H].

$$\% \text{ inhibition} = 1 - \frac{\text{average cpm (test compound} - \text{average cmp (blank)}}{\text{average cpm (control)} - \text{average cpm (blank)}}$$

$IC_{50}$ is defined as that concentration of compound which inhibits 50% of specific hydrolysis of [$^3$H]cAMP to [$^3$H] 5'AMP.

The ability of the compounds I or the pharmaceutically acceptable salts thereof to inhibit the production TNF and, consequently, demonstrate their effectiveness for treating disease involving the production of TNF is shown by the following in vitro assay:

Peripheral blood (100 mls) from human volunteers is collected in ethylenediaminetetraacetic acid (EDTA). Mononuclear cells are isolated by FICOLL/Hypaque and washed three times in incomplete HBSS. Cells are resuspended in a final concentration of 1×10$^6$ cells per ml in pre-warmed RPMI (containing 5% FCS, glutamine, pen/step and nystatin). Monocytes are plated as 1×10$^6$ cells in 1.0 ml in 24-well plates. The cells are incubated at 37° C. (5% carbon dioxide) and allowed to adhere to the plates for 2 hours, after which time non-adherent cells are removed by gentle washing. Test compounds (10 μl) are then added to the cells at 3–4 concentrations each and incubated for 1 hour. LPS (10 μl) is added to appropriate wells. Plates are incubated overnight (18 hrs) at 37° C. At the end of the incubation period TNF was analyzed by a sandwich ELISA (R&D Quantikine Kit). $IC_{50}$ determinations are made for each compound based on linear regression analysis.

The following Examples illustrate the invention.

EXAMPLE 1

1-(4-Fluorophenyl)-3-isopropyl-6-oxo-5-phenyl-4,6-dihydro-1H-pyrazolo[3,4-c]pyrrole A mixture of 3-hydroxy-4-isobutyryl-2-oxo-1-phenyl-2,5-dihydropyrrole (0.350 g, 1.43 mmole), 4-fluorophenylhydrazine hydrochloride (0.245 g, 1.50 mmole) and sodium methoxide (39 mg, 0.72 mmole) in ethanol (10 ml) was heated to reflux. After 16 hours the solvent was removed by rotory evaporation under reduced pressure, and the crude residue was chromatographed on a silica column using 1:3 ethyl acetate/hexane as eluent to give 210 mg of the title compound along with 80 mg of the 2-(4-fluorophenyl)-3-isopropyl-6-oxo-5-phenyl-4,6-dihydro-2H-pyrazolo[3,4-c] pyrrole regioisomer (M.P. 223°–224° C.). The title compound was recrystallized from ether to give a pale yellow solid. M.P. 150°–151° C.; $^1$H NMR (250 Mhz, CDCl$_3$) δ1.38 (d, J=7.0 Hz, 6H), 3.18 (heptet, J=7.0 Hz, 1H), 4.78 (s, 2H), 7.15 (dd, J=8.3, 9.1 Hz, 2H), 7.21 (m, 1H), 7.43 (t, J=7.9 Hz, 2H), 7.74 (d, J=7.8 Hz, 2H), 8.20 (dd, J=4.8, 9.1 Hz, 2H); MS m/z (M$^+$) 336.

EXAMPLES 2–18

Reaction of the appropriate hydrazine hydrochloride with the requisite 4-acyl-3-hydroxy-2-oxo-2,5-dihydropyrrole, analogous to the procedure of Example 1, afforded the following compounds of formula I wherein R$^1$, R$^2$ and R$^3$ are as defined below and R$^4$ is hydrogen.

(pentet, J=7.5 Hz, 1H), 6.61 (d, J=8.1 Hz, 2H), 6.74 (t, J=7.4 Hz, 1H), 7.29 (dd, J=7.5 and 8.4 Hz 2H); MS m/z 282.

EXAMPLE 20

1-(3,4-Dichlorophenyl)-3-methyl-5-methylenecyclopropyl-6-oxo-4,6-dihydro-1-H-pyrazolo[3,4-c]pyrrole A mixture of 2-(3,4-dichlorophenyl)-3-methyl-6-oxo-4,6-dihydro-1H-pyrazolo[3,4-c]pyrrole (0.20 g, 0.71 mmole) and 60% sodium hydride (0.24 g, 0.71 mmole) in anhydrous tetrahydrofuran (4 ml) was heated to reflux. After 45 minutes, the reaction mixture was cooled to room temperature

| Ex | R$^1$ | R$^2$ | R$^3$ | m.p. (°C.) | Mass Spectra or Analysis (calcd.) % C, % H, % N | Mass Spectra or Analysis (found) % C, % H, % N |
|---|---|---|---|---|---|---|
| 2 | iso-propyl | 4-methoxy-phenyl | 4-fluoro-phenyl | 140–142 | 69.03, 5.52, 11.49 MW 365.4 | 69.21, 5.36, 10.71 MS m/z 366 |
| 3 | iso-propyl | 4-methoxy-phenyl | cyclopentyl | 94–96 | 70.77, 7.42, 12.38 MW 339.4 | 70.86, 7.35, 11.00 MS m/z 340 |
| 4 | ethyl | phenyl | 4-fluoro-phenyl | 121–122 | 71.01, 5.02, 13.08 MW 321.4 | 70.88, 5.10, 12.59 MS m/z 322 |
| 5 | methyl | phenyl | 4-fluoro-phenyl | 176–177 | 70.35, 4.59, 13.67 | 70.11, 4.54, 13.43 |
| 6 | ethyl | phenyl | cyclopentyl | oil | 73.19, 7.17, 14.22 MW 295.4 | 72.83, 7.56, 13.39 Ms m/z 296 |
| 7 | iso-propyl | phenyl | cyclopentyl | oil | MW 309.4 | MS m/z 310 |
| 8 | iso-propyl | 3-methyl-phenyl | cyclopentyl | 96–97 | MW 323.4 | MS m/z 324 |
| 9 | iso-propyl | 3-methyl-phenyl | 4-fluoro-phenyl | 122–125 | MW 349.4 | MS m/z 350 |
| 10 | methyl | 3-benzoic acid | 4-fluoro-phenyl | 281–282 | 64.96, 4.02, 11.96 | 63.95, 4.05, 11.51 |
| 11 | methyl | 4-benzoic acid | 4-fluoro-phenyl | 323–325 | 64.96, 4.02, 11.96 | 64.56, 4.30, 11.75 |
| 12 | ethyl | phenyl | methyl | 56–57 | 69.69, 6.27, 17.41 | 69.80, 6.06, 17.41 |
| 13 | ethyl | phenyl | tert-butyl | 111.0 (sharp) | 72.06, 7.47, 14.83 | 71.68, 716, 14.78 |
| 14 | ethyl | phenyl | 4-methoxy-phenyl | 95–96 | 72.05, 5.74, 12.60 | 71.91, 5.48, 12.77 |
| 15 | ethyl | phenyl | methylene cyclopropyl | 95–96 | 72.57, 6.81, 14.94 | 72.21, 6.56, 14.85 |
| 16 | methyl | H | 3,4-dichloro-phenyl | 241–242 | 51.09, 3.22, 14.89 | 51.01, 3.11, 15.11 |
| 17 | ethyl | H | 4-fluoro-phenyl | 188–189 | MW 245.3 | MS m/z 246 |
| 18 | ethyl | H | cyclopentyl | 98–99 | 65.73, 7.81, 19.16 | 65.45, 7.76, 19.14 |

EXAMPLE 19

1-Cyclopentyl-3-ethyl-5-phenyl-4,6-dihydro-1H-pyrazolo[3,4-c]pyrrole

To a stirred solution of 1-cyclopentyl-3-ethyl-6-oxo-5-phenyl-4,6-dihydro-1H-pyrazolo[3,4-c]pyrrole (0.17 g, 0.58 mmole) in anhydrous ether (15 ml) was added lithium aluminum hydride (0.17 g, 4.6 mmole). The majority of the ether (12–13 ml) was then removed by distillation, and the remaining mixture diluted with toluene (25 ml) and heated to reflux over 24 hours. The mixture was cooled to 0° C. and cautiously treated with ice. The resulting mixture was filtered through celite, dried over sodium sulfate, filtered and concentrated under reduced pressure. The crude residue was chromatographed on a silica column using 1:9 ethyl acetate/hexane as eluent to give 100 mg of a colorless oil. $^1$H NMR (250 MHz, CDCl$_3$) δ1.26 (t, J=7.6 Hz, 3H), 1.65–2.25 (m, 8H), 2.67 (q, J=7.6 Hz, 2H), 4.35 (s, 2H), 4.45 (s, 2H), 4.53 and bromomethyl cyclopropane (0.11 g, 0.78 mmole) was added. The mixture was then warmed to 50° C. over 24 hours. The solvent was removed under reduced pressure and the residue recrystallized from a mixture of ethyl acetate and hexane to give 0.95 g of a yellow solid. M.P. 149.5°–152° C.; $^1$H NMR (250 MHz, CDCl$_3$) δ0.32–0.36 (m, 2H), 0.57–0.64 (m, 2H), 1.02–1.09 (m, 1h), 2.37 (s, 3H), 3.43 (d, J=7.1 Hz, 2H), 4.33 (s, 2H), 7.48 (d, J=8.8 Hz, 1H), 827 (dd, J=2.5 and 8.8 Hz, 1h), 8.48 (d, J=2.5 Hz, 1H); MS m/z 336.

EXAMPLES 21–24

Reaction of the appropriate alkylhalide with the requisite 6-oxo-4,6-dihydro-1H-pyrazolo[3,4-c]pyrrole, analogous to the procedure of Example 20, afforded the following compounds of formula I wherein R$^1$, R$^2$ and R$^3$ are as defined below and R$^4$ is hydrogen.

| Ex | R¹ | R² | R³ | m.p. (°C.) | Mass Spectra or Analysis (calcd.) % C, % H, % N | Mass Spectra or Analysis (found) % C, % H, % N |
|---|---|---|---|---|---|---|
| 21 | ethyl | methylene-cyclopropyl | 4-fluorophenyl | 94.0 (sharp) | 68.21, 6.06, 14.04 | 67.93, 5.99, 13.99 |
| 22 | ethyl | methyl | 4-fluorophenyl | 89–90 | 64.85, 5.44, 16.21 | 64.33, 5.18, 16.14 |
| 23 | ethyl | methyl | cyclopentyl | 54–55 | 66.92, 8.21, 18.01 | 67.18, 8.01, 18.22 |
| 24 | ethyl | methylene-cyclopropyl | cyclopropyl | oil | MW 273.4 | MS m/z 274 |

EXAMPLE 25

4,5-Dimethyl-3-ethyl-1-(4-fluorophenyl)-6-oxo-4,6-dihydro-1H-pyrazolo[3,4-c]pyrrole A mixture of 3-ethyl-1-(4-fluorophenyl)-6-oxo-4,6-dihydro-1H-pyrazolo[3,4-c]pyrrole (0.20 g, 0.82 mmole) and 60% sodium hydride (0.49 g, 1.2 mmole) in anhydrous tetrahydrofuran (4 ml) was heated to reflux. After 45 minutes the reaction mixture was cooled to room temperature and methyl iodide (0.29 g, 2.0 mmole) added. The mixture was then heated to reflux over 16 hours. The mixture was treated with methanol (1 ml) and the solvent removed under reduced pressure. The crude residue was chromatographed on a silica column using 1:4 ethyl acetate/hexane as eluent to give 0.12 g of the title compound. Recrystallization from ether/petroleum ether gave white crystals. M.P. 65°–65° C., Anal. calcd. for $C_{15}H_{16}FN_3O$: C, 65.92; H, 5.90; N, 15.37. Found: C, 66.15; H, 5.60; N, 15.53; MS m/z 274.

Preparation 1

3-Hydroxy-4-isobutyryl-2-oxo-1-phenyl-2,5-dihydropyrrole

To a stirred mixture of aniline (0.50 g, 5.4 mmole) and concentrated HCl (0.46 ml) in ethanol (2.5 ml) was added ethyl 5-methyl-2,4-dioxohexanoate (1.0 g, 5.4 mmole) and paraformaldehyde (0.25 g). After heating at reflux over 3 hours hot acetone (13 ml) was added and the resulting solution was cooled to room temperature and concentrated under reduced pressure. The residue was dissolved in 1N NaOH and extracted with methylene chloride. The aqueous layer was acidified to pH 1 with 3N HCl, extracted with methylene chloride, dried over sodium sulfate, filtered and concentrated under reduced pressure. Recrystallization from 10% ether in pet. ether gives 0.42 g of the title compound as a pale yellow solid. M.P. 162°–170° C.; ¹H NMR (250 MHz, CDCl₃) δ1.21 (d, J=6.8 Hz, 6H), 3.24 (heptet, J=6.8 Hz, 1H), 4.52 (s, 2H), 7.23 (m, 1H), 7.43 (t, J=8.0 Hz, 2H), 7.77 (d, J=7.8 Hz); MS m/z 246.

Preparations 2–7

Reactions of the appropriate 2,4-dioxoalkanoate with the requisite aryl amine, analogous to the procedure of Preparation 1, afforded the following compounds.

III $R^2-N$ structure with $R^4$, $R^1$, =O, OH groups

| Prep | R¹ | R² | m.p. °C. | Mass Spectra or Analysis (calcd.) % C, % H, % N | Mass Spectra or Analysis (found) % C, % H, % N |
|---|---|---|---|---|---|
| 2 | isopropyl | 4-methoxyphenyl | 168–172 | 65.44, 6.22, 5.09 | 65.27, 6.30, 4.75 |
| 3 | ethyl | phenyl | — | MW 231.25 | MS m/z 232 |
| 4 | methyl | phenyl | 180–184 | 66.35, 5.10, 6.45 | 66.47, 5.24, 5.44 |
| 5 | isopropyl | 3-methylphenyl | 155–158 | MW 259.31 | Ms m/z 260 |
| 6 | methyl | 3-benzoic acid | >275(dec) | * | * |
| 7 | methyl | 4-benzoic acid | >275(dec) | ** | ** |

*¹H nmr (250 MHz, DMSO-d₆) δ 2.42 (s, 3H), 4.46 (s, 2H), 7.54 (t, J=8.0 Hz, 1H), 7.74 (dd, J=1.1 and 7.8 Hz, 1H), 8.02 (d, J=8.1 Hz, 1H), 8.42 (s, 1H), 13.1 (broad s, 1H).
**¹H nmr (250 MHz, DMSO-d₆ δ 2.42 (s, 3H), 4.45 (s, 2H), 7.97 (s, 4H).

Preparation 8

4-Acetyl-3-hydroxy-2-oxo-2,5-dihydropyrrole

A solution of ethyl 2,4-dioxovalerate (1.13 g, 7.11 mmole), dimethylmethylene ammonium chloride (0.67 g, 7.11 mmole) and acetonitrile (3 ml) was stirred at 25° C. over 45 minutes. The resulting yellow homogeneous solution was then cooled to −40° C. and ammonia gas was bubbled through the mixture over 5 minutes, during which time a yellow solid precipitated out of solution. The stirred mixture was allowed to slowly warm to 5° C. over a period of 1 hour before addition of concentrated ammonium hydroxide (4 ml). After stirring for 1 hour, the mixture was concentrated under reduced pressure, diluted with 3N HCl (6 ml) and extracted with ethyl acetate (50 ml×10). The combined organics were dried over sodium sulfate, filtered and concentrated under reduced pressure to give 0.34 g of the title compound as a yellow amorphous solid. M.P. 178°–180° C. (dec); $^1$H nmr (250 MHz, DMSO-$d_6$) δ2.42 (s, 3H), 3.78 (s, 2H), 8.87 (s, 1H); Anal. calcd. for $C_6H_7NO_3$: C, 51.07; H, 5.00; N, 9.92. Found: C, 51.18; H, 5.23; N, 9.73.

Preparation 9

3-Hydroxy-2-oxo-4-propionyl-2,5-dihydropyrrole

Reaction of ethyl 2,4-dioxohexanoate with dimethylmethylene ammonium chloride and ammonia, analogous to the procedure in Preparation 8, gave the title compound as an amorphous solid. $^1$H nmr (250 MHz, DMSO-$d_6$) δ0.99 (t, J=7.3 Hz, 3H), 2.75 (q, J=7.3 Hz, 2H), 3.81 (s, 2H), 8.84 (s, 1H).

I claim:

1. A compound of the formula

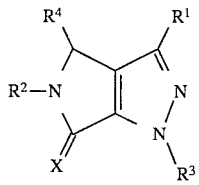

and pharmaceutically acceptable salts thereof;
wherein X is two hydrogens;
$R^1$ is hydrogen, $C_1$–$C_7$ alkyl, $C_2$–$C_3$ alkenyl, phenyl, $C_3$–$C_5$ cycloakyl or methylene($C_3$–$C_5$ cycloalkyl) wherein each alkyl, phenyl or alkenyl group may be substituted with one or two methyl, ethyl or trifluoromethyl, or up to three halogens;
$R^2$ and $R^3$ are each independently selected from the group consisting of hydrogen; $C_1$–$C_{14}$ alkyl; ($C_1$–$C_7$ alkoxy)($C_1$–$C_7$ alkyl)—; $C_2$–$C_{14}$ alkenyl; —$(CH_2)_n$($C_3$–$C_5$ cycloakyl) wherein n is 0, 1 or 2; a $(CH_2)_n$ ($C_4$–$C_7$ heterocyclic group) wherein n is 0, 1 or 2, containing as the heteroatom one of oxygen, sulphur, sulphonyl or $NR^5$ wherein $R^5$ is hydrogen, or $C_1$–$C_4$ alkyl; or a group of the formula

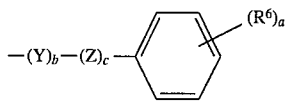

wherein a is an integer from 1 to 4; b and c are 0 or 1; $R^6$ is hydrogen, hydroxy, $C_1$–$C_5$ alkyl, $C_2$–$C_5$ alkenyl, $C_1$–$C_5$ alkoxy, $C_3$–$C_6$ cycloalkoxy, halogen, trifluoromethyl, nitro, $CO_2R^7$, $CONR^7R^8$, $NR^7R^8$, or $SO_2NR^7R^8$ wherein $R^7$ and $R^8$ are each independently hydrogen or $C_1$–$C_4$ alkyl; Z is oxygen, sulphur, sulphonyl or $NR^9$ wherein $R^9$ is hydrogen or $C_1$–$C_4$ alkyl; and Y is $C_1$–$C_5$ alkylene or $C_2$–$C_6$ alkenylene which may be substituted with one or two $C_1$–$C_7$ alkyl or $C_3$–$C_7$ cycloakyl; wherein each said alkyl, alkenyl, cycloalkyl, alkoxyalkyl or heterocyclic group may be substituted with one to fourteen substituents $R_{10}$ selected from the group consisting of methyl, ethyl, trifluoromethyl and halogen; and $R^4$ is hydrogen, $C_1$–$C_7$ alkyl, phenyl, $C_3$–$C_5$ cycloalkyl, or methylene ($C_3$–$C_5$ cycloalkyl) wherein each alkyl or phenyl group may be substituted with one or two methyl, ethyl or trifluoromethyl, or up to three halogens.

2. A compound according to claim 1 wherein $R^1$ is $C_1$–$C_7$ alkyl.

3. A compound according to claim 1 wherein $R^4$ is hydrogen.

4. A compound according to claim 1 wherein $R^3$ is $C_1$–$C_6$ alkyl; phenyl substituted by one or two halogen; cyclopentyl, or methylenecyclopropyl.

5. A compound according to claim 1 wherein $R^2$ is hydrogen, $C_1$–$C_6$ alkyl, or phenyl which may be substituted with $C_1$–$C_5$ alkyl, $C_1$–$C_5$ alkoxy or COOH.

6. A compound according to claim 1 wherein $R^1$ is $C_1$–$C_7$ alkyl, $R^4$ is hydrogen, $R^3$ is $C_1$–$C_6$ alkyl; phenyl substituted by one or two halogen; cyclopentyl, or methylenecyclopropyl, and $R_2$ is hydrogen, $C_1$–$C_6$ alkyl or phenyl which may be substituted with $C_1$–$C_5$ alkyl, $C_1$–$C_5$ alkoxy or COOH.

7. A pharmaceutical composition for the inhibition of phosphodiesterase (PDE) type IV and the production of tumor necrosis factor (TNF) comprising a pharmaceutically effective amount of a compound according to claim 1 and a pharmaceutically acceptable carrier.

8. A method for the inhibition of phosphodiesterase (PDE) type IV and the production of tumor necrosis factor (TNF) comprising administering to a patient an effective amount of a compound according to claim 1.

9. A method of treating or preventing a condition selected from the group consisting of asthma, arthritis, bronchitis, chronic obstructive airways disease, psoriasis, allergic rhinitis, dermatitis and other inflammatory diseases, septic shock and other diseases involving the production of TNF comprising administering to a patient an effective amount of a compound according to claim 1.

* * * * *